United States Patent [19]

Blaney

[11] 3,964,486

[45] June 22, 1976

[54] DISPOSABLE DIAPER CONTAINING AMMONIA INHIBITOR

[75] Inventor: Ted Lee Blaney, West Chester, Ohio

[73] Assignee: The Procter & Gamble Company, Cincinnati, Ohio

[22] Filed: Jan. 27, 1975

[21] Appl. No.: 544,471

Related U.S. Application Data

[63] Continuation-in-part of Ser. No. 498,497, Aug. 19, 1974, abandoned, which is a continuation-in-part of Ser. No. 406,426, Oct. 15, 1973, abandoned.

[52] U.S. Cl. ............................. 128/284; 128/290 R; 424/28
[51] Int. Cl.² ........................................ A61F 13/16
[58] Field of Search ............ 128/284, 287, 290, 270, 128/285, 296, 156, 286; 424/27, 28, 76

[56] References Cited

UNITED STATES PATENTS

| | | | |
|---|---|---|---|
| 2,418,907 | 4/1947 | Schreiber | 128/290 R |
| 2,542,909 | 2/1951 | Dewet | 128/290 X |
| 2,643,969 | 6/1953 | Mahon | 128/284 |
| 2,837,462 | 6/1958 | Morin | 128/290 R |
| 3,592,194 | 7/1971 | Duncan | 128/287 |
| 3,707,148 | 12/1972 | Bryce | 128/284 |
| 3,794,034 | 2/1974 | Jones, Sr. | 128/290 R |

*Primary Examiner*—John D. Yasko
*Attorney, Agent, or Firm*—Monte D. Witte; Fredrick H. Braun; John V. Gorman

[57] ABSTRACT

A disposable pad comprising an absorbent substrate having incorporated therein adipic acid in a quantity sufficient to inhibit ammonia formation and concommitant diaper rash.

8 Claims, No Drawings

DISPOSABLE DIAPER CONTAINING AMMONIA INHIBITOR

CROSS REFERENCE TO RELATED APPLICATION

This application is a continuation-in-part of copending application Ser. No. 498,497 filed Aug. 19, 1974, now abandoned which was a continuation-in-part of application Ser. No. 406,426 filed Oct. 15, 1973, now abandoned.

BACKGROUND OF THE INVENTION

This invention relates to disposable diapers and incontinent pads. More particularly, it relates to disposable diapers which are characterized in their content of an agent which inhibits ammonia formation caused by the decomposition of urine.

It is known that ammonia dermatitis or "diaper rash" is caused or is potentiated by free ammonia generated in a urine-wet diaper in contact with an infant's skin. The ammonia is formed by bacterial enzymatic decomposition of urinary urea by a wide variety of fecal bacteria such as *Bacterium ammoniagenes*, a saprophytic gram positive bacillus, and *Proteus vulgaris*, a gram negative bacillus. In view of this knowledge, the art has proceeded along essentially two lines in the prevention of diaper rash. In one approach, the prior art has attempted to prevent the liberation of ammonia from urine-wet diapers by means of chemical agents which trap the gaseous ammonia generated by the ammonia producing bacteria. Such ammonia immobilizing agents include inter alia weak organic and inorganic acids such as acetic, citric, and boric acid, capable of forming ammonium salts. The ammonia immobilizing agent may be impregnated throughout the absorptive wadding or located in discrete gas permeable sachets enfolded within the diaper.

Another approach to the prevention of diaper rash has been to incorporate a bacteriostatic agent in the diaper structure. Various carboxylic acids have been used for this purpose. U.S. Pat. No. 3,707,148 issued to Bryce on Dec. 26, 1972, for example, describes the use of carboxylic acids to inhibit microbial growth and ammonia formation. This patent discloses disposable diaper structures impregnated with citric, malic, maleic, malonic, succinic, tartaric, and fumaric acids. It has now been discovered that several of the specified carboxylic acids, citric acid for example, dissolve too rapidly when the diaper is wetted with urine, such that the urine as it wicks out to the edge of the diaper is relatively concentrated in acid, and the center of the diaper loses its protection against ammonia formation. As a result, skin irritation can occur at the diaper margins due to the excessively low pH at this point. Other carboxylic acids, e.g., fumaric acid, while dissolving more slowly relative to wicking rate, still produce excessively low pH at the edge of the diaper because they are relatively strong acids and there are no basic ions for buffering due to ion exchange of the urine as it wicks through the diaper.

Thus, a suitable acid for use in the present context must have a slow dissolution rate relative to the wicking time and should be a relatively weak acid to the end that it is capable of maintaining a pH level throughout the diaper that is compatible with the babies' skin pH and effective at inhibiting ammonia generation.

SUMMARY OF THE INVENTION

It has now been discovered that adipic acid is uniquely suited to the purposes of this invention by virtue of its specific combination of bacteriostatic, solubility, dissolution rate and weakly acidic properties. Thus, the present invention is a disposable diaper and incontinent pad comprising an absorbent substrate having incorporated therein an effective amount of adipic acid and, optionally, an effective amount of sodium adipate.

It is an object of this invention to provide an improved disposable diaper which safely and effectively reduces ammonia generation and concommitant diaper rash in use.

DETAILED DESCRIPTION OF THE INVENTION

The particular diaper structure is not critical to the practice of the present invention. The only essential structural element is the absorbent substrate in a pad or disposable sheet configuration. Representative examples of suitable diaper structures are fully described in the following U.S. Pat. No. Re. 26,151, (Duncan et al., Jan. 31, 1967); U.S. Pat. No. 3,592,194 (Duncan, July 13, 1971) and U.S. Pat. No. 3,489,148 (Duncan et al., Jan. 13, 1970); which are incorporated herein by reference. A preferred disposable diaper for the purpose of this invention comprises an absorbent core; a topsheet superposed or co-extensive with one face of said core; a liquid impervious backsheet superposed or co-extensive with the face of said core opposite the face covered by said topsheet; said backsheet most preferably having a width greater than that of said core thereby providing side marginal portions of said backsheet which extend beyond said core, said marginal portions being folded around and on top of the edges of said absorbent core. The diaper is preferably folded in a box pleat configuration.

The topsheet can be made in part or completely of synthetic fibers such as Verel, polyolefin, rayon, or the like, or of natural fibers such as cotton. The fibers are typically bound together by a polymeric binder such as polyacrylate. This sheet is substantially porous and permits a fluid to readily pass therethrough into the underlying absorptive core. The topsheet can be made either hydrophobic or hydrophilic depending upon the choice and treatment of fiber and binder used in the construction thereof. The topsheet construction is generally disclosed in U.S. Pat. No. 2,905,176 (Davidson, Sept. 22, 1959); U.S. Pat. No. 3,063,452 (Del Guercio, Nov. 13, 1962); and U.S. Pat. No. 3,113,570 (Holliday, Dec. 10, 1963), incorporated herein by reference.

The absorbent core or substrate can be constructed from highly absorbent essentially hydrophilic fiber aggregates which act as a reservoir for excreted waste fluid. For example, this layer can consist of piles of creped cellulose wadding. Fibers which are useful herein can be classified according to origin as wood, rag, cotton linters, straw, or esparto and according to manufacture as mechanical, chemical, semi-chemical, unbleached, semi-bleached or bleached. Preferred absorbent substrates are prepared from wood, cotton or cotton linters.

The backsheet of the diaper can be constructed, for example, from a thin, plastic film of polyethylene, polypropylene, or other flexible moisture impeding material which is substantially water impervious.

Adipic acid is, of course, a staple item of commerce. Technical grade adipic acid, prepared by oxidizing cyclohexanol with concentrated nitric acid, is widely available in commercial quantities. The acid can be incorporated into the diaper structure by diverse methods which will be readily apparent to those skilled in the art. For example, the adipic acid can be dispersed in a skin innocuous (non-irritating) or volatile carrier such as water, ethanol, or the like and applied to the diaper topsheet, to the absorbent core, or to the core side of the backsheet, by spraying, dipping, printing or otherwise contacting the selected substrate with the acid solution.

Although the above-described methods of incorporation are suitable under many conditions and for most uses, it has been found that the unique solubility properties of adipic acid, while desirous in the context of the instant invention, impede application of solubilized adipic acid. Accordingly, it has been discovered that adipic acid, in solution, can preferably be applied by combining the adipic acid with small quantities, i.e., from about 1 to about 10 percent by weight, of azelaic acid, or by incorporating the acid in the absorbent hydrophilic substrate as a hot melt. The addition of azelaic acid increases the hot water solubility of the acids system thus facilitating spray applications. Moreover, it has been found that the addition of minor amounts of azelaic acid results in improved adhesion of adipic acid to the chosen substrate and improved resistance to urine wash-out.

Finally, the difficulties, previously described, of applying adipic acid in liquid form to the selected substrate can be overcome by the use of dry or granular metering processes. Such processes are well known in the solids handling art. In general, suitable dry metering processes comprise a reservoir which holds the solid to be dispersed and a means of uniform distribution. The particles to be dispersed are preferably in the size range of 25 to 100 mesh and most preferably 25 to 40 mesh.

The concentration of adipic acid employed in the diaper should be sufficient to provide a urine pH level of from about 3.5 to about 5.5 during use throughout the diaper upon wetting with urine. In order to inhibit the growth of microorganisms which generate ammonia by acting upon urea, a urine pH level of about 3.5 to 5.5 should be maintained. Below a pH of about 3.5 skin irritation can occur because the urine is rendered too acidic. Above about pH 5.5, gram negative as well as gram positive bacteria will grow with the accompanying generation of ammonia.

One of the factors cooperating with the adipic acid of this invention to maintain the in-use pH within the desired range is the buffering capacity of the urine absorbed into the diaper. Infant urine frequently has a lower buffering capacity than adult urine with the result that, when adipic acid is used alone, the pH of the wet diaper occasionally drops below the desired 3.5 lower limit. Accordingly, a preferred diaper embodiment of this invention contains as an added component a buffering compound. Sodium adipate is a suitable buffering compound. Mixtures of adipic acid and sodium adipate can be incorporated into the diaper structure by the same methods used for incorporating adipic acid alone.

Normally, the adipic acid, when it is used alone, is incorporated into the diaper structure in an amount of from about 0.5 to about 4.0 grams, preferably from 0.7 to 3 grams per diaper. Diapers designated "daytime diapers" in the art preferably contain from about 0.7 to 2.0 grams. Diapers which by virtue of their greater bulk and absorptive capacity are designated "nighttime diapers" or "toddlers' diapers" and are intended for overnight use preferably contain from about 1.00 to 3.0 grams per diaper.

When a mixture of adipic acid and sodium adipate is incorporated into a diaper structure, the weight of the sodium adipate in the mixture is from about 25 to about 40 percent of the weight of adipic acid in excess of 0.6 gram in each diaper. The amounts of the two components used in each diaper are normally from about 0.7 gram adipic acid and about 0.02 gram sodium adipate to about 4 grams adipic acid and about 1.4 grams sodium adipate, preferably from about 0.7 gram adipic acid and about 0.03 gram sodium adipate to about 3 grams adipic acid and about 0.8 gram sodium adipate. Diapers designated daytime diapers in the art preferably contain from about 0.7 gram adipic acid and about 0.03 gram sodium adipate to about 2.0 grams adipic acid and about 0.5 gram sodium adipate. Nighttime diapers and toddlers' diapers preferably contain from about 1.00 grams adipic acid and about 0.2 gram sodium adipate to about 3 grams adipic acid and about 0.8 gram sodium adipate.

The following examples more thoroughly detail the use of suitable processes to apply adipic acid to an absorbent substrate, and are not intended to limit the invention herein disclosed.

EXAMPLE I

Disposable diapers, prepared according to U.S. Pat. No. Re. 26,151, consisting of a thin polyethylene backsheet attached to an absorbent airfelt pad, were treated with from 0.3 gram to about 3.0 grams of adipic acid and succinic acids as follows:

Adipic acid and succinic acid, respectively, were sieved to obtain 40–80 mesh particles. The particles were spread using a dry granular spreader (Industrial Dispensing Machine, Model Coat-O-Matic 16 DI), in varying amounts, as a 5½ inch uniform band to the back or polyethylene side of the airfelt pad starting about 2½ inches from the front of the diapers.

Following application of the acid to the diapers, 25 ml. aliquots of 37°C adult urine, having a pH of 6.0 and a titratable acid content of 15 milliequivalents per liter, were poured into the center of each diaper 5 inches from the top over a 10 second period. After 5 minutes storage at 32°C, slight pressure was applied to the wetted area for one minute with an eight-inch watch glass. The diapers were allowed to set for 19 minutes at 32°C, after which the pH readings were taken on a 1 inch grid over all wetted areas of the diapers.

Finally, the above procedure was repeated on each diaper using a second 25 ml. aliquot of urine.

The results for the initial and subsequent urine loading are summarized in Table I below.

TABLE 2

| Acid Applied | Quantity Applied (grams) | % of Wetted Diaper Having pH of 3.5 - 5.5 | | % of Wetted Diaper Having pH <3.5 | | % of Wetted Diaper Having pH >5.5 | |
|---|---|---|---|---|---|---|---|
| | | 1st Wetting | 2nd Wetting | 1st Wetting | 2nd Wetting | 1st Wetting | 2nd Wetting |
| Adipic | 0.3 | 80 | 67 | 0 | 0 | 20 | 33 |
| | 0.5 | 97 | 80 | 0 | 0 | 3 | 20 |
| | 0.7 | 97 | 78 | 0 | 0 | 3 | 21 |
| | 0.9 | 100 | 77 | 0 | 0 | 0 | 23 |
| | 1.5 | 100 | 94 | 0 | 0 | 0 | 6 |
| | 1.7 | 100 | 90 | 0 | 0 | 0 | 10 |
| | 1.9 | 100 | 96 | 0 | 0 | 0 | 6 |
| | 2.7 | 100 | 97 | 0 | 0 | 0 | 4 |
| | 2.9 | 100 | 93 | 0 | 0 | 0 | 0 |
| Succinic | 0.3 | 91 | 66 | 3 | 0 | 6 | 34 |
| | 0.6 | 87 | 66 | 10 | 9 | 3 | 25 |
| | 0.9 | 93 | 76 | 6 | 15 | 0 | 9 |
| | 1.1 | 65 | 71 | 35 | 23 | 0 | 6 |
| | 1.5 | 60 | 48 | 40 | 36 | 0 | 16 |
| | 1.7 | 55 | 70 | 45 | 27 | 0 | 0 |
| | 2.4 | 40 | 51 | 60 | 45 | 0 | 4 |

The results summarized above demonstrate that at levels of 0.5 gram or more of acid applied per diaper, adipic acid maintains the urine pH in the diaper in the desired range of from 3.5–5.5., while succinic acid, a homologous acid, fails to closely maintain the desired pH level. Further, the few diapers treated with adipic acid which did not maintain the desirable pH range over the entire wetted area never had wetted areas falling below the 3.5 acidic pH, while a significant portion of the succinic acid treated diaper area exceeded the maximum tolerable acidic level.

EXAMPLE II

A disposable diaper is prepared according to the teachings of U.S. Pat. No. Re 26,151 consisting of a thin backsheet of polyethylene attached to a pad of absorbent airfelt (matting of cellulose fibers). Combined backsheet and absorbent wadding is overlaid with a compliant porous, hydrophobic, non-woven fabric web diaper liner (topsheet) having a weight of approximately 17 grams per square yard and which comprises 2.0 denier rayon and contains 28 percent by weight of a thermoplastic binder. The combined laminated structure is approximately 15 × 18 inches and is folded into a box pleat configuration by means of a multiplicity of longitudinal folds.

A hot melt of adipic acid is prepared by heating adipic acid above 152°C. The molten adipic acid is applied to the absorbent pad prior to its assemblage in the above diaper by metering the acid melt with a positive displacement pump and by spraying the acid melt, at a rate of 1 gram/diaper, onto the absorbent wadding using two fan-shaped spray nozzles, one directed to the front of the diaper and one directed to the center. The spray rate of each nozzle is adjusted to around 90 grams/minute under a positive pressure of about 10 to 20 lbs./sq. inch.

Comparable results are secured when the molten adipic acid is applied to the topsheet, backsheet, airfelt, absorbent pad or onto a tissue insert by roller printing techniques well known in the art.

EXAMPLE III

Disposable diapers in accordance with this invention were prepared as follows:

Wood pulp fluff was air laid on a single-ply paper tissue containing Kymene No. 557 as a wet-strength resin. Immediately thereafter, an adipic acid/water slurry (55 percent by weight adipic acid; 0.15 percent by weight polysaccharide xanthan gum ((Keltrol)); balance distilled water) was metered with a positive displacement pump and sprayed onto the wood pulp fluff as in Example II. A second single-ply paper tissue was then laid over the adipic acid impregnated wood pulp fluff thereby enveloping it between two layers of paper tissue.

A rayon topsheet was affixed to the paper tissue containing wet strength resin with adhesive. The composite was cut to the following dimensions:

Daytime diapers — 11⅜× 15½ inches
Nighttime diapers — 11⅞× 16 inches respectively, and a polyethylene sheet was affixed to the non-wet strength resin tissue side with adhesive. The diapers were then folded into a box pleat configuration and packaged for use.

Analysis revealed that the daytime diapers prepared as above contained an average of about 0.9 grams of adipic acid per diaper. The nighttime diapers contained about 1.1 grams/diaper.

To determine the pH distribution samples of the above diapers were wetted in the center with 50 ml. of adult urine (pH 6.0). Most of the wetted diaper was found to be within the pH range of 4.0 to 5.5. The pH at the diaper margins did not go below about pH 3.75. In contrast, diapers containing citric or fumaric acid in place of adipic acid were tested in like manner and the resultant pH distributions were found to range from 5.4 to a low of 2.3 and 3.05, respectively, at the diaper margins. In use, the adipic acid treated diapers yield a significant reduction in ammonia formation and concommitant diaper odor.

EXAMPLE IV

Disposable diapers, prepared according to U.S. Pat. No. Re. 26,151, consisting of a thin polyethylene backsheet attached to an absorbent airfelt pad, were each treated with 0.9 gram adipic acid and 0.1 gram sodium adipate as follows:

The adipic acid, in particle size range of 25–40 mesh, was spread in a 5.5 inch uniform band on the polyethylene side of the airfelt pad starting about 2.5 inches from the front of each diaper. The dry granular spreader described in Example I was used. The sodium adipate was sprayed on the airfelt pad as a 25 percent (weight) water solution.

Following application of the mixture to the diapers, they were wetted with 60 ml. aliquots of 37°C adult urine which had been diluted to such an extent that it required 10 milliequivalents acid per liter to reduce the pH from 6.0 to 4.0 and thereby represented infant urine in buffering capacity. Over the whole wetted surface of the diaper, the pH was within the range of about 3.8 to about 4.3.

While each of the specific examples described above involves disposable diaper structures, it will be apparent to those skilled in the art that the benefits and advantages of this invention can be realized when the adipic acid impregnated absorbent core is employed in disposable absorptive pads designed for use by babies and incontinent individuals.

And while the foregoing discussion concerning the optional buffering compound has emphasized the use of sodium adipate, it is to be understood that any buffering compound, or any compound which reacts with adipic acid to form an alkali metal salt of adipic acid, is suitable for use in this invention. Any such added compound, which can be present in amounts equivalent to those noted for sodium adipate, should possess very low toxicity and skin irritant properties.

What is claimed is:

1. In a disposable diaper comprising an absorbent core, a topsheet superposed or co-extensive with one face of said core, and a liquid impervious backsheet superposed or co-extensive with the face of said core opposite the face covered by said topsheet, the improvement comprising incorporating therein from about 0.5 to about 4.0 grams of adipic acid.

2. A disposable diaper in accordance with claim 1 which contains from about 0.7 to about 3.0 grams of adipic acid.

3. A disposable pad comprising an absorbent core having incorporated therein an amount of adipic acid sufficient to suppress ammonia formation therein when wetted with urine.

4. A disposable pad in accordance with claim 3 containing from about 0.5 to about 4.0 grams of adipic acid.

5. A disposable pad in accordance with claim 4 in a diaper configuration.

6. In a disposable diaper comprising an absorbent core, a topsheet superposed or co-extensive with one face of said core, and a liquid impervious backsheet superposed or co-extensive with the face of said core opposite the face covered by said topsheet, the improvement comprising incorporating therein from about 0.72 to about 5.4 grams of a mixture of adipic acid and sodium adipate wherein said adipic acid is present to the extent of at least about 0.7 gram and said sodium adipate is present in an amount of from about 25 to about 40 percent of the amount of said adipic acid in excess of 0.6 gram.

7. A disposable diaper in accordance with claim 6 which contains from about 0.7 gram adipic acid and about 0.03 gram sodium adipate to about 3 grams adipic acid and about 0.8 gram sodium adipate.

8. In a disposable diaper comprising an absorbent core, a topsheet superposed or co-extensive with one face of said core, and a liquid impervious backsheet superposed or co-extensive with the face of said core opposite the face covered by said topsheet, the improvement comprising incorporating therein from about 0.72 to about 5.4 grams of a mixture of adipic acid and a buffering compound wherein said adipic acid is present to the extent of at least about 0.7 gram and said buffering compound is present in an amount of from about 25 to about 40 percent of the amount of said adipic acid in excess of 0.6 gram.

\* \* \* \* \*